United States Patent [19]

Fox

[11] 4,344,842

[45] * Aug. 17, 1982

[54] REACTIVE IRON OXIDE AGENTS FOR SCAVENGING HYDROGEN SULFIDE FROM HYDROCARBON LIQUIDS

[75] Inventor: Irwin Fox, 37 Meadowbrook Country Club Estates, Ballwin, Mo. 63011

[73] Assignees: Irwin Fox, Ballwin, Mo.; Alvin Samuels, New Orleans, La.; David Samuels, St. Louis, Mo.

[*] Notice: The portion of the term of this patent subsequent to Jan. 20, 1998, has been disclaimed.

[21] Appl. No.: 221,897

[22] Filed: Dec. 31, 1980

Related U.S. Application Data

[63] Continuation-in-part of Ser. No. 44,026, May 31, 1979, Pat. No. 4,246,244, which is a continuation-in-part of Ser. No. 963,797, Nov. 27, 1978, Pat. No. 4,246,243.

[51] Int. Cl.$^3$ ............................................. C10G 29/16
[52] U.S. Cl. .................................... 208/244; 210/722; 210/749; 585/820; 585/850
[58] Field of Search ................. 423/225, 231; 210/702, 210/719, 721, 722, 916, 749; 208/244; 585/820, 850

[56] References Cited

U.S. PATENT DOCUMENTS

| | | | |
|---|---|---|---|
| 4,089,809 | 5/1978 | Farrior | 423/231 X |
| 4,113,606 | 9/1978 | Mulaskey | 208/244 |
| 4,201,751 | 5/1980 | Holter et al. | 423/231 X |
| 4,246,244 | 1/1981 | Fox | 423/231 |

FOREIGN PATENT DOCUMENTS 48-11321  12/1973  Japan ................................... 208/244

Primary Examiner—Earl C. Thomas
Attorney, Agent, or Firm—Jerome A. Gross

[57] ABSTRACT

Iron oxide particles composed of a crystalline phase of Fe$_2$O$_3$, Fe$_3$O$_4$ and combinations thereof together with an amorphous Fe$_2$O$_3$ moiety or portion and having a surface area of at least 3.5 m$^2$/g are useful for scavenging hydrogen sulfide from substantially anhydrous non-aqueous liquids, particularly substantially anhydrous hydrocarbon liquids, for example, kerosene.

4 Claims, No Drawings

REACTIVE IRON OXIDE AGENTS FOR SCAVENGING HYDROGEN SULFIDE FROM HYDROCARBON LIQUIDS

CROSS-REFERENCE TO RELATED APPLICATIONS

This application is a continuation-in-part of Ser. No. 44,026, filed May 31, 1979, now U.S. Pat. No. 4,246,244 issued Jan. 20, 1981, and also of Ser. No. 963,797, filed Nov. 27, 1078, co-pending herewith, now U.S. Pat. No. 4,246,243 issued Jan. 20, 1981, each being continuations-in-part of prior applications as therein set forth, entitled "PROCESS FOR SCAVENGING HYDROGEN SULFIDE FROM HYDROCARBON GASES, co-pending herewith, their as to their common disclosed subject matter, the benefit of the filing dates thereof is hereby claimed.

FIELD OF THE INVENTION

This invention relates to the use of particulate from oxides for scavenging hydrogen sulfide from non-aqueous liquids such as liquid hydrocarbons.

BACKGROUND OF THE INVENTION

The presence of hydrogen sulfide in liquid kerosens, for example, is unacceptable even in small amounts. Yet as well as this Applicant can determine, little has been accomplished in developing any simple scavenging treatment for such non-aqueous liquids.

In U.S. Pat. No. 4,008,775, issued Feb. 22, 1977, and assigned to the same assignee as the present application, there is described a process in which specific porous iron oxides are used in drilling muds, primarily aqueous drilling muds to scavenge hydrogen sulfide ($H_2S$) released from a well in the course of a drilling operation. These iron oxides are described as having an ideal composition of substantially $Fe_3O_4$, a particle size of about 1.5 to 60 microns and a surface area of at least ten times as great as magnetite ($Fe_3O_4$) particles of equal size.

In co-pending application Ser. No. 44,026, filed May 31, 1979, and assigned to the same assignee as the present application, the same iron oxide (referred to as Compound A) as described in said patent is further characterized as having an amorphous $Fe_2O_3$ (non-crystalline) moiety together with an $Fe_3O_4$ crystalline phase. Further, in said application, other iron oxide particles (referred to as Compounds B and C), specifically, iron oxide waste dusts from open hearth or basic oxygen furnace steel-making operations, are described as being somewhat similar to the iron oxide particles of said patent in that they also have large surface areas and have an amorphous moiety of $Fe_2O_3$ and an $Fe_3O_4$ crystalline phase. However, they also have an $Fe_2O_3$ crystalline phase. Still other iron oxide particles (referred to as Compound D) having a high surface area and an amorphous $Fe_2O_3$ moiety and a crystalline $Fe_2O_3$ phase are described in said application.

In the present application the designations Compounds A, B, C and D are intended to designate the same compounds identified and characterized in said co-pending application, the entire description of which is hereby incorporated by reference.

In said co-pending application, it is also described that the aforesaid iron oxide particles are useful for scavenging $H_2S$ from hydrocarbon gases by bubbling such gases through a water suspension of such iron oxide particles, and a proces for practicing such scavenging of $H_2S$ is claimed in said application. Said aplication also describes that in experiments utilizing a Parr pressure bomb apparatus, the recovery of sulfur-containing solids was fully as efficient where anhydrous diesel fuel was substituted for water in forming a test slurry of the type designated Compounds AD, residual water content of dessicated samples was less than 0.2%. However, this descriptive matter is not claimed in said co-pending application. Said description goes on to point out that "the results were not to be expected, in view of Simon and Reichelt [Z. Amerg. Allg. Chem. 319:962 (1964)] which teaches that iron oxide reacts with hydrogen sulfide by being first hydrated to FeOOH; that the hydrogen sulfide becomes ionized to form $HS^-$ and $H^+$; and the reaction proceeds between the FeOOH and the $HS^-$ at an optimum water content of 18.0%".

It is described in U.S. Pat. No. 4,089,809, issued May 16, 1978, that $H_2S$ can be removed from producer gas by passing the gas (at very high temperatures) through a bed of pellets composed of silica and $Fe_2O_3$; and U.S. Pat. No. 4,201,751, issued May 6, 1908, describes that $H_2S$ can be removed from coke oven gas by contacting the gas with a fluidized bed of particles of perlite containing steel-making dust comprising $Fe_2O_3$ and an alkaline material such as lime under very turbulent conditions. However, applicant is unaware of any published information which teaches that $H_2S$ can be scavenged from substantially non-aqueous liquid systems using iron oxides, much less the iron oxides which have been found to be useful in the practice of the present invention.

OBJECTS OF THE INVENTION

It is an important object of the present invention to provide a process for scavenging hydrogen sulfide from non-aqueous liquids, in the substantial absence of water, utilizing dry or substantially dry particles of certain iron oxides as the scavenging agent.

It is a further object of the present invention to provide a process for scavenging hydrogen sulfide from a hydrocarbon liquid which process produces only stable reaction products.

SUMMARY OF THE INVENTION

The present invention provides a process for scavenging $H_2S$ from a substantially anhydrous non-aqueous liquid containing same, which comprises intimately contacting such liquid with dry or substantially dry particles of hydrogen sulfide-reactive iron oxide particles having a surface area of at least 3.5 $m^2/g$ and composed substantially of a crystalline phase of $Fe_2O_3$, $Fe_3O_4$ and combinations thereof together with an amorphous $Fe_2O_3$ moiety or portion. The contacting should be such that the $H_2S$ in the liquid is contacted with such iron oxide particles. The amount of iron oxide particles used is generally such that the $H_2S$ content (generally above 20 ppm) (parts per million) of the liquid is reduced to a predetermined level, for example, less than 10 ppm and preferably to 4 ppm or less. The temperature of the liquid used is generally between 10° C. and 50° C., but may be higher or lower depending primarily on the boiling point of the liquid at higher temperatures, and the viscosity of the liquid at lower temperatures.

A variety of stable reaction products are formed in carrying out the process depending primarily on contact time, the properties of the specific iron oxide particles used and to some extent on the amount of water, if any, present in the liquid being treated and/or in the iron oxide particles. In general, if the iron oxide particles have an $Fe_3O_4$ crystalline phase and an $Fe_2O_3$ amorphous moiety, but no $Fe_2O_3$ crystalline phase, the crystalline reaction product will be stable and comprise a mixture of $FeS_2$ (pyrite) and $Fe_3S_4$ (greigite); the ratio of one to the other being primarily dependant on the contact time and the water content of the liquid and/or particles. On the other hand, if the iron oxide particles used have a crystalline phase of $Fe_2O_3$ and an amorphous $Fe_2O_3$ moiety, but no crystalline $Fe_3O_4$ phase, the crystalline reaction products will be stable and comprise primarily $FeS_2$, although some $Fe_3S_4$ may also be formed. By "stable reaction products" is meant reaction products such as S°, $FeS_2$, $Fe_3S_4$ and other stable non-FeS species, as described in said co-pending application.

DESCRIPTION OF THE PREFERRED EMBODIMENTS

In carrying out the processes of the present invention, any substantially anhydrous non-aqueous liquid containing $H_2S$ may be used although it is preferred to employ a substantially anhydrous hydrocarbon liquid, that is a liquid composed of one or more compounds consisting of carbon and hydrogen atoms, and such compound or compounds may be saturated or unsaturated, that is, contain —c=c or —c≡c bonds. Hydrocarbon liquids such as those obtained from producing wells or earth formations often contain $H_2S$ in concentrations in excess of 20 ppm, and the present processes are designed to reduce the $H_2S$ content thereof to an acceptable level so that the liquid can be used in refining operations without poisoning catalytic materials or in combustion processes without emitting deleterious quantities of noxious $SO_2$ fumes.

The terms "substantially anhydrous non-aqueous liquids" or "substantially anhydrous hydrocarbon liquids" as used herein are intended to identify liquids which are free of water or which only contain the normal amounts of water present in the liquid as a result of low or high atmospheric humidity conditions existing during the storage of the liquid, and, therefore, such amounts will vary to some extent depending on the hydrophilic or hydrophobic characteristics of the liquid. In general, the water content of the liquid will seldom exceed 2% by weight, and in most cases will be in the range of from about 0.0001% to about 0.05% by weight of water. In accordance with the present invention, $H_2S$ can be successfully scavenged from non-aqueous liquids or hydrocarbon liquids even though they are essentially anhydrous or contain such small amounts of water.

The liquid is preferably intimately contacted with the iron oxide particles by incorporating the particles into the liquid and subjecting the resulting mixture to high shear mixing or agitation so as to expose the surface area of the particles to as much solid-liquid interface as possible thereby enabling the particles to contact the $H_2S$ in the liquid. By operating in this manner, it is also possible to scavenge the $H_2S$ from the liquid as quickly and as efficiently as the reactivity of the particles permit. Generally, the contact time will be less than four hours, and usually satisfactory scavenging of the $H_2S$ will occur within a period of 30–150 minutes.

As noted previously herein, the iron oxide particles employed are dry or substantially dry prior to incorporation in the liquid, by which is meant that the particles only contain an amount of water such as the particles will have after manufacture and/or after storage in a low or high humidity atmosphere prior to use. In any event, even though the particles may contain some water they are free-flowing, and appear and feel to be dry particulates of matter. In general, the water content of the particles will seldom be in excess of 8% by weight, and in most cases will be in the range of from about 0.001 to about 1% by weight. Usually, the water content of the iron oxide particles will be partially what may be termed "free" water; that is, water which is picked up from the atmosphere under storage conditions, and partially what may be termed "bound" water; that is, water contained in the particles after rather vigorous drying, for example, drying under a vacuum at 100°–110° C. for 24 hours. The amount of "free" water is usually from about 1.5 to about 6 times greater than the amount of "bound" water.

It has been found that two classes of iron oxide particles have unexpectedly higher $H_2S$ reactive capacity and rates of reaction than other iron oxides within the scope of this invention, and, accordingly, are preferred. These preferred classes of iron oxide particles are as follows:

(1) A class of iron oxide particles having a surface area of at least 3.5 $m^2/g$, a kinetic "V" value of at least 1000 and which are composed of an $Fe_3O_4$ crystalline phase, substantially free of crystalline $Fe_2O_3$, and an amorphous $Fe_2O_3$ moiety. Said particles are described in said U.S. Pat. No. 4,008,775 and in said co-pending application (under the designation Compound A). Particularly preferred are specific iron oxide particles, designated Compound A in said co-pending application, and also herein, the pertinent properties of which are disclosed in the specific examples herein. This class of particles has the theoretical capacity to react with more $H_2S$ than any other iron oxides of which I am aware; and (2) A class of iron oxide particles having a surface area of at least 3.5 $m^2/g$, a kinetic "K" value of at least 2000 and which are composed of an $Fe_2O_3$ crystalline phase, substantially free of crystalline $Fe_3O_4$, and an amorphous $Fe_2O_3$ moiety. Such particles are prepared by the conventional high temperature oxidation of ferrous sulfate. Other properties of such class of particles are described in said co-pending application and in my co-pending application Ser. No. 185,155, filed Sept. 8, 1980, and assigned to the same assignee as the present application. Particularly preferred are iron oxide particles, designated Compound D in said co-pending applications, and also herein, the pertinent properties of which are described in the specific examples herein.

The temperature of the liquid during contacting of with the iron oxide particles is not believed to be critical but is preferably such that a satisfactory reaction rate between the $H_2S$ and the particles is obtained and the reaction products are stable, that is, do not readily decompose to form $H_2S$, and so that the liquid is not so viscous as to preclude intimate mixing of the liquid and particles. The stability of the reaction products can be determined by their acid stability as disclosed in said co-pending application Ser. No. 44,026, filed May 31, 1979. A preferred temperature range for admixture of the liquid and particles is from about 15° C. to about 40° C.

The following specific examples are given to illustrate the present invention and the practice thereof, but are not to be construed to limit the scope thereof.

EXAMPLE I

A. Description of Materials Used:

(1) Hydrocarbon liquid used was kerosene having a boiling point range of 80°–165° C. at 76 Omm of pressure and a flash point range of 65°–85° C.

(2) Dry kerosene is the kerosene of (1) dried with molecular sieve material to a water content of 48 mg per kilogram of kerosene or 0.0048% water by weight.

(3) Wet kerosene is the kerosene of (1) mixed with deionized water and allowed to separate into two layers from which the water layer was removed giving a kerosene containing 89 mg water per kilogram of kerosene or 0.0089% water by weight.

(4) Compound A is composed of iron oxide particles having a particle size of 6–8 mm, a surface area of 10 $m^2/g$, a kinetic "K" value (determined as hereinafter described) of 2000 and containing a crystalline phase of $Fe_3O_4$, substantially free of $Fe_2O_3$ crystalline phase, and an amorphous $Fe_2O_3$ moiety. This material had a water content of 2940 mg per kilogram of iron oxide or 0.29% water by weight.

(5) Dry Compound A is the same as Compound A except that it has been dried in a circulating oven at 100°–110° C. for 48 hours to a moisture content of 60 mg per kilogram of iron oxide or 0.006% by weight of water.

B. Description of Equipment Used:

Slurry Reactor:

All reactions described herein were performed in a water-cooled, glass blender reactor (Lab Glass, Inc., Vineland, NJ) attached to a Waring blender. The reactor had an internal diameter of 3⅛" and was 10½" high. The blender reactor was fitted with a gasketed lid supplied with various ground glass fittings. The blender contents were mixed by a four blade turbine assembly, located at the base of the reactor, at 10000 rpm. Hydrogen sulfide gas was supplied to the reactor from a lecture bottle regulated to 0.42 kg/cm² (6 psig). A flowmeter was used to control the delivery of the gas to the reactor discharge tube. The tube outlet was located below the surface of the blender contents. Gas exiting the reactor was measured by a flowmeter and excess hydrogen sulfide was absorbed in a caustic trap.

Infusion rates of hydrogen sulfide gas were controlled to allow a minimum of 4.0 g $H_2S$/hour to enter the reactor. The reactor contained 500 ml of kerosene and 28.4 g of iron oxide material (20 lbs/bbl), and the contents were mantained at a temperature of 22° C. to 25° C.

Several combinations of iron oxide materials were used with the dry and wet kerosene. All test conditions were carried out in duplicate.

To determine the completion of each run, the gas exiting the reactor was measured by a flowmeter. The reaction was stopped when the exit hydrogen sulfide flow was equal to the inlet hydrogen sulfide flow. At this point, the reaction was considered to have reached capacity.

At capacity, a sample of slurry was removed from the reactor and diluted ten-fold with dry kerosene, and the sample was placed in a sealed container. This dilution lowered the $H_2S$ partial pressure in the sample container and provided a convenient method to retain the sample for analysis. The delay between sampling and analysis was less than 30 minutes.

Three samples were analyzed for hydrogen sulfide. One sample contained slurried solids and hydrocarbon from the reactor. A second sample was centrifuged and the supernatent was analyzed. A third sample was taken from the caustic trap. These analyses were used to obtain a material balance and determine the quantity of hydrogen sulfide reacted with the iron oxide.

After the reaction, a large portion of the reacted solids were separated by centrifugation and rinsed three times with acetone to remove residual kerosene. The solids were then dried at 100°–110° C. for 24 hours and analyzed for reaction products by x-ray crystallography.

Table I, which follows, shows the conditions used in the equipment for scavenging $H_2S$ employing various combinations of dry kerosene, wet kerosene, Compound A and dry Compound A, and the $H_2S$ reactive capacities of Compound A under these conditions.

TABLE 1

| EXP. NO. | Reactant Combination Kerosene | Reactant Combination Compound A | Infused $H_2S$ (g) | Unreacted $H_2S$ in Slurry and Trap (g) | Reacted $H_2S$ (g) | Time at Capacity (hours) | Infusion Rate (g/h) | Breakthrough Time (hours) | Breakthrough Capacity ($\frac{g\ H_2S}{g\ cpd\ A}$) | Average Capacity ($\frac{g\ H_2S}{g\ cpd\ A}$) |
|---|---|---|---|---|---|---|---|---|---|---|
| 1 | D (1) | W (3) | 18.0 | 2.8 | 15.2 | 3.53 | 5.1 | 2.22 | 0.54 | 0.55 |
|   | D | W | 18.8 | 3.5 | 15.3 | 3.72 | 5.05 | 2.07 | 0.56 | |
| 2 | W (2) | W | 16.5 | 3.3 | 13.2 | 3.27 | 5.05 | 1.25 | 0.46 | 0.465 |
| 3 | W | W | 15.3 | 2.0 | 13.3 | 2.67 | 5.73 | 0.67 | 0.47 | |
| 4 | W | D (4) | 15.4 | 2.6 | 12.8 | 2.74 | 5.62 | 1.44 | 0.45 | 0.43 |
| 5 | W | D | 14.9 | 2.8 | 12.1 | 2.50 | 5.95 | 0.78 | 0.43 | |
| 6 | W | D | 13.3 | 2.0 | 11.3 | 2.57 | 5.18 | 0.78 | 0.40 | |
| 7 | D | D | 14.4 | 1.8 | 12.6 | 2.09 | 6.89 | 0.48 | 0.44 | 0.44 |
| 8 | D | D | 13.3 | 2.0 | 11.3 | 2.63 | 5.06 | 1.18 | 0.40 | |
| 9 | D | D | 11.6 | 1.4 | 10.2 | 2.29 | 5.06 | 0.67 | 0.36 | |

TABLE 1-continued

| EXP. NO. | Reactant Combination Kerosene | Compound A | Infused $H_2S$ (g) | Unreacted $H_2S$ in Slurry and Trap (g) | Reacted $H_2S$ (g) | Time at Capacity (hours) | Infusion Rate (g/h) | Breakthrough Capacity Time (hours) | Average Capacity $\left(\dfrac{g\ H_2S}{g\ cpd\ A}\right)$ |
|---|---|---|---|---|---|---|---|---|---|
| 10 | D | D | 24.6 | 4.6 | 20.0 | 5.0 | 4.92 | Not Measured | 0.66 |

(1) D represents dry kerosene
(2) W represents wet kerosene
(3) W represents Compound A
(4) D represents Dry Compound A Table 2, which follows, shows the analytical results obtained with regard to unreacted iron oxide and x-ray diffraction analysis of the reaction products obtained in the experimental runs of Table 1.

TABLE 2

| EXP. NO. | Reactant Combination Remaining Iron Oxide (%) | $FeS_2$ (%) | $FeS_4$ (%) | Ratio $\dfrac{Fe_3S_4}{FeS_2}$ | % Total Sulfur in Crystalline Products | % Total Sulfur (Amorphous and Crystalline) | Capacity $\left(\dfrac{g\ H_2S}{g\ Cpd\ A}\right)$ |
|---|---|---|---|---|---|---|---|
| 1* | <10% | 19 ± 2 | 5** | 20/80 | 12.4 | 40.0 | 0.56 |
| 2* | 25-35% | 13 ± 2 | 17** | 55/45 | 14.4 | 27.9 | 0.46 |
| 3* | 35%** | 13 ± 2 | 17** | 55/45 | 14.4 | 35.5 | 0.47 |
| 4 | 50-55% | 31 ± 1 | 13** | 30/70 | 22.4 | 27.7 | 0.45 |
| 5 | 20%** | 33 ± 3 | 28** | 45/55 | 30 | 36.9 | 0.43 |
| 6 | 20%** | 34 ± 1 | 32** | 50/50 | 32.3 | 30.3 | 0.40 |
| 8 | 50%** | 21 ± 2 | 17** | 45/55 | 18.7 | 28.9% | 0.40 |
| 10 | 5% | 78 ± 2 | 20** | 20/80 | 50.7** | — | 0.66 |

*Quantitative results are altered by large amount of amorphous material present.
**About It will be noted from the experimental results of TABLES 1 and 2 that the $H_2S$ reactive capacity of iron oxide containing free water (Experiments 13) is higher than that of the dried oxide (Experiments 4 and 8), with the exception of Experiment 10 in which a larger amount of $H_2S$ was infused, whereas an increase in water content of the kerosene actually lowers the reactive capacity of such oxide (compare Experiment 1 and Experiments 2 and 3). On the other hand, the $H_2S$ reactive capacity of either Compound A or dry Compound A is of somewhat the same magnitude whether the kerosene contains more or less water (Experiments 2 and 6). The analytical results indicate that both $FeS_2$ and $Fe_3S_4$ are formed in varying amounts depending on the reactant combinations used. However, both of these products are stable and do not release $H_2S$ in the presence of air and are also "acid stable" as that term is used and defined in said co-pending application, Ser. No. 44,026, filed May 31, 1979.

EXAMPLE II

A. Description of Materials Used:

(1) The kerosene used was the same as described in items (1), (2) and (3) of Example I.

(2) Compound D is composed of iron oxide particles having a particle size somewhat smaller than Compound A (of Example I), a surface area of 4 $m^2/g$, a kinetic "K" value of 4000 and containing a crystalline phase of $Fe_2O_3$, substantially free of crystalline $Fe_3O_4$, and an amorphous $Fe_2O_3$ moiety. This material has a water content of 250 mg per kilogram of iron oxide or 0.025% by weight of water.

(3) Dry Compound D is the same as Compound D except that it was dried prior to use at 105° C. for 24 hours to a water content of 170 mg per kilogram of iron oxide or 0.017% by weight of water.

B. Description of Equipment Used:

The equipment used was the same as described in Example I. Table 3, which follows, shows the conditions used in the equipment for scavenging $H_2S$ employing various combinations of dry kerosene, wet kerosene, dry Compound D, and the $H_2S$ reactive capacities of Compound D under these conditions.

TABLE 3

| Exp. No. | Reactant Combinations Kerosene | Compound D | Infused $H_2S$ (g) | Unreacted $H_2S$ in Slurry and trap (g) | Reacted $H_2S$ (g) | Time at capacity (hours) | Infusion Rate (g/h) | Capacity $\left(\dfrac{g\ H_2S}{g\ cpd\ D}\right)$ |
|---|---|---|---|---|---|---|---|---|
| 11. | D(1) | D(3) | 19.6 | 1.41 | 18.2 | 4.89 | 4.79 | 0.64 |
| 12. | W(2) | D | 22.2 | 1.5 | 20.7 | 4.43 | 5.01 | 0.73 |

(1) D is dry kerosene
(2) W is wet kerosene
(3) D is dry Compound D

Note: Although no experiment was run using Compound D prior to drying, an experiment essentially identical to Experiment 11 but utilizing 5% of water, based on kerosene, gave a capacity of 0.62 indicating that free moisture in the particles would not influence reactivity significantly.

Table 4, which follows, shows the analytical results obtained with regard to unreacted iron oxide and x-ray diffraction analyses of the reaction products obtained in the experimental runs of Table 3.

TABLE 4

| Exp. No. | Remaining Iron Oxide (%) | $FeS_2$ (%) | $Fe_3S_4$ (%) | Ratio $\frac{Fe_3S_4}{FeS_2}$ | Total Sulfur (%) | Capacity $\left(\frac{g\ H_2S}{g\ cpd\ D}\right)$ |
|---|---|---|---|---|---|---|
| 11. | 20 | 46 ± 5 | 4–5* | 10/90 | 22.4 | 0.64 |
| 12. | 25–40 | 44 ± 5 | 6* | 10/90 | 26.3 | 0.73 |

*About

It will be noted from Table 3 and Table 1 that Compound D has a higher $H_2S$ reactive capacity than Compound A even though the theoretical reactive capacity of Compound A is higher than that of Compound D. Also the experimental runs indicate that the $H_2S$ reactive capacity of Compound D is not significantly affected by the water content therein, and that, in contrast to Compound A, the capacity of Compound D is increased somewhat if the water content of the kerosene is higher. Further, Table 4 shows that the reaction product formed when using Compound D under various water content conditions is substantially $FeS_2$ whereas the reaction products obtained with Compound A (Table 2) contain varying amounts of $FeS_2$ and $Fe_3S_4$ under such conditions.

EXAMPLE III

A. Description of Materials Used:

(1) The kerosene used was the same as described in items (1), (2) and (3) of Example I.

(2) Compound C is composed of iron oxide particles having a particle size somewhat smaller than Compound A (of Example 1), a surface area of 4 $m^2/g$, a kinetic "K" value of 100 and containing an $Fe_2O_3$ and $Fe_3O_4$ crystalline phase and an amorphous $Fe_2O_3$ moiety. This material has a water content of 676 mg per kilogram of iron oxide or 0.068% by weight of water.

(3) Dry Compound C is the same as Compound C except that it was dried at 100°–110° C. for 24 hours prior to use, and has a water content of 560 mg per kilogram of oxide or 0.056% by weight of water.

(4) Magnetite is magnetite ore particles which are composed substantially of an $Fe_3O_4$ crystalline phase and an amorphous $Fe_3O_4$ moiety and have a surface area of about 1 $m^2/g$ and a kinetic "K" value of less than 1.0. This material was received as a water slurry, centrifuged to remove as much water as possible and dried in vacuum at 100°–110° C. for 24 hours prior to use. It has a water content of 100 mg per kilogram of magnetite or 0.001% by weight of water.

B. Description of Equipment Used:

The equipment used was the same as that described in Example I.

Table 5, which follows, shows the conditions used in the equipment for scavenging $H_2S$ employing various combinations of wet kerosene, dry kerosene, dry Compound C and magnetite, and the $H_2S$ reactive capacities of these iron oxides under these conditions.

TABLE 5

| Exp. No. | Reactant Combinations Kerosene | Reactant Combinations Iron Oxide | Infused $H_2S$ (g) | Unreacted $H_2S$ in Slurry and Trap (g) | Reacted $H_2S$ (g) | Time at Capacity (hours) | Infusion Rate (g/h) | Capacity $\left(\frac{g\ H_2S}{g\ Iron\ oxide}\right)$ |
|---|---|---|---|---|---|---|---|---|
| 13. | D(1) | Dry Cpd. C | 8.5 | 4.17 | 4.33 | 1.67 | 5.1 | 0.15 |
| 14. | D | Magnetite | 15.1 | 2.76 | 10.78 | 2.54 | 5.93 | 0.38 |
| 15. | W(2) | Magnetite | 3.5 | 2.27 | 1.28 | 0.84 | 4.2 | 0.05 |

(1)D represents dry kerosene
(2)W represents wet kerosene

An experiment was also run as in Experiment 13 but adding 5% by weight of water to the reactants with the result that the capacity of Compound C was increased to 0.34. These experiments indicate that Compound C has considerably less capacity than Compounds A and D under substantially dry conditions (compare with Tables 1 and 3) whereas the capacity of magnetite was substantially reduced when the kerosene contained more water.

Table 6, which follows, shows the analytical results obtained with regard to unreacted iron oxide and x-ray diffraction analyses of the reaction products obtained in the experimental runs of Table 5.

TABLE 6

| Exp. No. | Remaining Iron Oxide (%) | $FeS_2$ (%) | $Fe_3S_4$ (%) | Ratio $\frac{Fe_3S_4}{FeS_2}$ | Total Sulfur (%) | Capacity $\left(\frac{g\ H_2S}{g\ iron\ oxide}\right)$ |
|---|---|---|---|---|---|---|
| 13. | 95 | 5 ± 1 | — | — | 2.7 | 0.15 |
| 14. | 85 | 14 ± 4 | — | — | 7.5 | 0.38 |
| 15. | 85 | 5 ± 1 | — | — | 2.7 | 0.05 |

As noted previously herein, it is disclosed in said co-pending application Ser. No. 44,026 that in experiments utilizing a Parr pressure bomb apparatus, recovery of sulfur-containing solids was fully as efficient (compared to water slurry systems), where anhydrous diesel fuel was substituted for water in forming a test slurry of desicated iron oxide of the type designated Compounds A-D, residual water content of desicated samples was less than 0.2%.

As to the kinetic "K" value in the above description in the pH range 8-10, the derived rate law for Compound A is as follows:

$$\frac{d[S_t]}{dt} = K \times [S_t]^2 \times [H^+]^{1.06} \times [A]$$

wherein [$S_t$] is sulfide concentration in ppm, t is time in minutes, $d[S^t]/dt$ is the instantaneous rate of change of dissolved sulfide concentrations, [$H^+$] is hydrogen iron concentration and [$A$] is iron oxide concentration (lb./bbl). K is the rate constant in min.$^{-1}$ ppm$^{-1}$ cm$^2 \times$ 1/mole and equal to approximately 2000. At Ph 8–10, the derived rate law agrees closely with Rickard's analysis of the reaction of hydrated iron oxide (ferric hydroxide) and hydrogen sulfide [Am. J. Sci., 274:941 (1974)]. When [$S_t$] and [$H^+$] are measured intermittently during the course of continuous acid reaction the substitution of observed [$S_t$] and [$H^+$] values into the rate law equation above yields apparent K values which define relative differences in reaction rates among different iron oxides.

I claim:

1. The process for scavenging hydrogen sulfide from a hydrocarbon liquid containing said sulfide which comprises contacting the hydrogen sulfide in said liquid with dry or substantially dry iron oxide particles having a surface area of at least 3.5 m$^2$/g and composed of a crystalline phase of $Fe_2O_3$, $Fe_3O_4$ and combinations together with an amorphous $Fe_2O_3$ moiety, said particles being used in an amount sufficient to reduce the hydrogen sulfide concentration in said liquid to a predetermined level.

2. The process according to claim 1, wherein the contacting is carried out for a period of time sufficient to form stable reaction products including $FeS_2$ and $Fe_3S_4$.

3. The process for scavenging hydrogen sulfide from a substantially anhydrous hydrocarbon liquid containing said sulfide in amounts in excess of 20 ppm which comprises contacting the hydrogen sulfide in said liquid with iron oxide particles having a surface area of at least 3.5 m$^2$/g, a kinetic "K" value of at least 1000 and composed of a crystalline phase of $Fe_3O_4$, substantially free of crystalline $Fe_2O_3$ phase, and an amorphous $Fe_2O_3$ moiety and containing from about 0.001 to about 0.5% by weight of water, said particles being used in an amount sufficient to reduce said hydrogen sulfide content to less than 10 ppm and said contacting being carried out for a period of time sufficient to form stable reaction products including $FeS_2$ and $Fe_3S_4$.

4. The process for scavenging hydrogen sulfide from a substantially anhydrous hydrocarbon liquid containing said sulfide in amount in excess of 20 ppm which comprises contacting the hydrogen sulfide in said liquid with iron oxide particles having a surface area of at least 3.5 m$^2$/g, a kinetic "K" value of at leat 1000, a water content of from about 0.001 to about 0.5% by weight and composed of a crystalline phase of $Fe_2O_3$, substantially free of an $Fe_3O_4$ crystalline phase, and an amorphous $Fe_2O_3$ moiety, said particles being used in an amount sufficient to reduce said hydrogen sulfide content to less than 10 ppm and said contacting being carried out for a period of time sufficient to form stable reaction products including $FeS_2$ and $F_3S_4$.

* * * * *

UNITED STATES PATENT AND TRADEMARK OFFICE
CERTIFICATE OF CORRECTION

PATENT NO. : 4,344,842
DATED : August 17, 1982
INVENTOR(S) : Irwin Fox

It is certified that error appears in the above—identified patent and that said Letters Patent is hereby corrected as shown below:

```
In column 1, line 12, delete "1078" and insert ---1978---.
In column 1, line 17, delete "their" and insert ---and---.
In column 1, line 21, delete "from" and insert ---iron---.
In column 1, line 26, delete "kerosens" and insert ---kerosene---.
In column 2, line 22, delete "1908" and insert ---1980---.
In column 4, line 26, delete "V" and insert ---K---.
In column 12, line 22, delete "leat" and insert ---least---.
In column 12, line 30, delete "F_3S_4" and insert ---Fe_3S_4---.
```

Signed and Sealed this

Nineteenth Day of October 1982

[SEAL]

Attest:

GERALD J. MOSSINGHOFF

Attesting Officer

Commissioner of Patents and Trademarks